(12) United States Patent
Yu et al.

(10) Patent No.: US 6,358,498 B1
(45) Date of Patent: Mar. 19, 2002

(54) PERSONAL CARE PRODUCT IN THE FORM OF A FREE-STANDING STICK

(75) Inventors: Wei H. Yu, Montclair; Rupali A. Kulkarni, Bridgewater; Ralph Macchio, Sparta, all of NJ (US); Salvatore J. Barone, Staten Island, NY (US); Antonietta Corrigan, Somerville, NJ (US)

(73) Assignee: Coty B.V., Haarlem (NL)

( * ) Notice: Subject to any disclaimer, the term of this patent is extended or adjusted under 35 U.S.C. 154(b) by 0 days.

(21) Appl. No.: 09/642,489

(22) Filed: Aug. 18, 2000

(30) Foreign Application Priority Data

Aug. 19, 1999 (DE) ............................ 199 40 221

(51) Int. Cl.[7] .................... A16K 6/00; A16K 7/00; A16K 7/025
(52) U.S. Cl. ......................... 424/64; 424/401
(58) Field of Search .................... 424/64, 401

(56) References Cited

U.S. PATENT DOCUMENTS 4,980,192 A    12/1990   Finkel ................... 426/631

FOREIGN PATENT DOCUMENTS

| GB | 2 014 852 |   | 9/1979 |
| GB | 2014852 A | * | 9/1979 |
| WO | WO 98/08484 |   | 3/1998 |
| WO | WO 98/19652 |   | 5/1998 |

OTHER PUBLICATIONS

Shiseido, KK, JP–A–1068–405, Abstract 86–129439/20, Nov. 9, 1984, Japan.

* cited by examiner

Primary Examiner—Thurman K. Page
Assistant Examiner—S. Howard
(74) Attorney, Agent, or Firm—Collard & Roe, P.C.

(57) ABSTRACT

A new personal care product in the form of a free-standing stick comprises an inner core with cosmetic ingredients and an solid outer shell adhering to the inner core, in which the outer shell is wax-free and contains at least solid proteins, liquid polyols or solutions of polyols, solid polyols, emollients and additional cosmetic auxiliary materials and active ingredients. The outer surface does not transfer pigment through brief contact with the skin and is also not sticky.

12 Claims, No Drawings

PERSONAL CARE PRODUCT IN THE FORM OF A FREE-STANDING STICK

The invention concerns a new cosmetic personal care product as well as an agent for improving the appearance of the body, in which the agent is available as a free-standing stick.

There are a range of cosmetic products known which are available on the market in stick form, such as lip sticks, deodorant sticks, personal care sticks, etc. All of these sticks have in common the fact that they are essentially developed on a wax basis in order to achieve the appropriate stability at ambient temperature. A disadvantage of these products is often their stickiness and/or the undesirable transfer of colorant, for example in the case of lip sticks, on areas of skin where a colouring is not desired, for example on the fingers.

The invention is based on the task of developing a free-standing cosmetic stick as a personal care product, the outer surface of which does not transfer pigment through brief contact with the skin and which is also not sticky.

In accordance with the invention, the new personal care product in the form of a free-standing stick which comprises an inner core with cosmetic ingredients and an solid outer shell adhering to the inner core, in which the outer shell is waxfree and contains at least the following ingredients, in relation to the total amount of the outer shell, (a) one or more solid proteins in the range of 0.5 to 50 weight %;

(b) one or more liquid polyols or solutions of polyols in the range of 0.2 to 15 weight %;

(c) one or more solid polyols in the range of 0.5 to 80 weight (d) one or more emollients in the range of 1 to 90 weight %;

(e) additional cosmetic auxiliary materials and active ingredients in the range of between 0 and 80 weight %.

As solid proteins for the outer shell, proteins are used which include soy protein, milk protein, oat protein, silk protein, pea protein, wheat protein, placental protein, collagen, rice protein, vegetable protein, wheat gluten, wheat germ protein, whey protein, potato protein, sweet almond protein, rice bran protein, yeast protein, keratin, corn protein, spinal protein, conchiorin protein, elastin, serum protein and their derivatives, which include hydrolyzed derivatives, ester derivatives, hydrogenated derivatives; and mixtures thereof.

The amount of these solid protein materials preferably is in the range of 5 to 50% by weight, especially 10 to 50% by weight. A further preferred range is 20 to 40% by weight.

As liquid polyols or solutions of polyols for the outer shell such materials can be used which include straight or branched chained hydrocarbon compounds containing at least two hydroxyl groups on the carbon skeleton. They are for instance sorbitol, propylene glycol, arachidyl glycol, benzyl glycol, butylene glycol, butoxydiglycol, C14-18 glycol, C15-18 glycol, C18-30 glycol, C20-30 glycol, caprylyl glycol, ceteareth-60 myristyl glycol, cetyl glycol, diethylene glycol, dimethoxyglycol, dipropylene glycol, ethoxydiglycol, glycol, hexacosyl glycol, hexylene glycol, hydrogenated talloweth-60 matristyl glycol, lauryl glycol, methoxydiglycol, neopentyl glycol, octacosanyl glycol, PEG-10 propylene glycol, pentylene glycol, PEG-75-PEG-300 hexylene glycol, stearyl glycol, thiodiglycol, triethylene glycol, tripropylene glycol, glycerin; and mixtures thereof.

The amount of these liquid polyols or solutions of polyols total preferably is in the range of 1.0 to 10% by weight.

Further solid polyols for the outer shell are used in the composition of the present invention. Polyols are compounds which contain three or more hydroxyl groups per molecule including polysaccharides. As solid polyols, such materials can be used which include diglycerin, fructose, glucose, inositol, lactitol, lactose, maltitol, maltose, mannitol, sorbitol, sucrose, polyglycerin, starches such as corn starch, soy starch, wheat starch, oat starch, potato starch, rice starch, tapico starch; and modified starch and their derivatives; cellulose and cellulose derivatives; and mixtures thereof.

The amount of these solid polyols total preferably is in the range of 15 to 70% by weight especially 25 to 70% by weight. A further special range is 30 to 70% by weight or 2 to 40% by weight.

As emollients for the outer shell such materials as fats, oils, fatty alcohols, fatty acid ethers and esters as well as mixtures of these can also be used. Examples arecocoa butter, shea butter, goat butter, illipe butter, jojoba butter, mango butter, avocado butter, shorea sponoptera butter, pentadesma butytacea butter, vegetable oil, castor oil, cottonseed oil, coconut oil, C12-18 triglycerides, jojoba oil, lanolin, menhadenn oil, milk lipids, mink oil, olive oil, orange roughly oil; palm kernel oil, palm oil, peanut oil, rapeseed oil, soybean oil, shark liver oil, and their glyceryl esters and derivatives, such as hydrogenated oils, and mixtures thereof.

The amount of the emollients preferably is in the range of 2 to 40% by weight.

In addition the outer shell can contain pigments colorants, such as staining dyes and usual pigments. Preferred pigments include calcium, barium and aluminium lakes, iron oxides, titanium dioxide and mica.

The outer shell can also contain active skin-care ingredients and if necessary further ingredients such as anti-oxidation agents, UV filters, moisturising agents, protective agents, perfume, etc.

The inner core of the personal-care product contains wax, emollients, active skin-care ingredients and if necessary additional ingredients such as colorants, pigments, anti-oxidation agents, UV filters, moisturising agents, protective agents, perfume and such accompanying substances known to specialists in this field.

As wax for the inner core, a wax can be used which is selected from the wax group consisting of candelilla, beeswax, carnauba, spermaceti, montan, ozokerite, ceresin, paraffin, modifies beeswax, bayberry, castor waxes, synthetic waxes, microcristalline waxes; and mixtures thereof.

The amount of waxes is in the range of 5 to 90% by weight, preferably from about 10 to 30% by weight, most preferably from about 10 to about 20% by weight, in relation to the composition of the inner core.

The emollients of the inner core can be the same as in the conventional lipsticks or the same as in the outer shell. Emollient means skin conditioning agents including emollients, humectants, occlusive and other miscellaneous ingredients which condition the skin as disclosed in the CTFA. The amount of emollients in the inner core is in the range of 1 to about 90% by weight, preferably from about 10 to 80% by weight, more preferably from about 20 to about 70% by weight, and most preferably from about 40 to about 60% by weight, in relation to the composition of the inner core.

The active skin-care ingredients which are water soluble and water insoluble forms can be added to the sticks. Said ingredients include fat soluble vitamins such as vitamin A and E, sunscreens and pharmaceutically active ingredients. These skin care active ingredients include zinc oxide, chamomile oil, ginkgo biloba extract, proglutamic acid, salts or esters; sodium hyaluronate; 2-hydroxyoctanoic acid; sulfur; salicylic acid; carboxymethyl cysteine; and mixtures thereof. The same active skin care ingredients can be used in the outer coating.

The amount of the skin care active ingredients in the inner core is in the range of 0,0001 to about 10% by weight, in relation to the composition of the inner core. The same amount is also usable in the outer shell.

The amount of colorants in the inner core is in the range of 0 to about 35% by weight, preferably from about 1 to about 20 % by weight, in relation to the composition of the inner core. The same amount is also usable in the outer shell.

The thickness of the outer shell in relationship to the inner core lies between approximately 0.1 to 1:1, preferably at about 0.2 to about 0.5, referring to the radius of the inner core.

The new personal care product with the non-wax based outer shell has a solid surface, does not flow even at higher temperatures and thus does not adhere to the fingers by brief contact. Corresponding to the further ingredients it is antiaging, soothing, moisturizing and provides nutrients for the skin.

It was found that only the presence of proteins together with polyols and fat/oils leads to a product with a stiff consistence resulting to a free-standing stick. The personal product can be used on lips, face, eyes and bodies, preferably on lips.

A special characteristic of the invention is the heat stability of the outer shell, which is especially shown in the fact that the drop melting point of the outer shell above 105° C. while the drop melting points of conventional cosmetic sticks are about 60° C.

The manufacture of the stick with inner core is done in the usual way, for example with a casting plant according to EP-B-0712593.

The invention will be illustrated by the following examples. All figures are percent by weights if not other mentioned.

Example 1

| Outer shell | |
| --- | --- |
| Phase A | |
| Shea butter | 18 |
| Hydrogenated palm oil | 8 |
| Palm oil | 10 |
| Castor oil | 13 |
| Soy protein | 15 |
| Modified corn starch | 10 |
| Nylon-12 | 4 |
| Sericite GMS-4C | 15 |
| Pigment | 6 |
| Phase B | |
| Glycerin | 1 |

Example 2

| Outer shell | |
| --- | --- |
| Phase A | |
| Illipe butter | 20 |
| Hydrogenated palm oil | 6 |
| Polyisobutylene | 5 |
| Tridecyl trimellitate | 10 |
| PEG-4 Diheptanoate | 4 |
| Isopropylpalmitate | 6 |
| Castor oil | 8 |
| Soy protein | 15 |
| Cellulose PH-105 | 10 |
| Sericite GMS-4C | 10 |
| Pigment | 5 |
| Phase B | |
| Glycerin | 1 |

Example 3

| Outer shell | |
| --- | --- |
| Phase A | |
| Illipe butter | 27 |
| Soy protein | 15 |
| Lauroyl lysine | 1 |
| Nylon-12 | 10 |
| Silk mica | 10,5 |
| Pigment | 10 |
| Castor oil | 20 |
| Phase B | |
| Glycerin | 6,5 |

Example 4

| Outer shell | |
| --- | --- |
| Phase A | |
| Shea butter | 26 |
| Hydrogenated palm oil | 7,5 |
| Palm oil | 7,5 |
| Castor oil | 15 |
| Silk mica | 10 |
| Modified corn starch | 10 |
| Silk powder | 15 |
| Pigment | 5 |
| Phase B | |
| Glycerin | 4 |

Example 5

| Outer shell | |
| --- | --- |
| Phase A | |
| Shea butter | 20 |
| Hydrogenated palm oil | 8 |
| Palm oil | 10 |
| Castor oil | 7 |
| Hydrogenated castor oil | 1 |
| Cetearyl methicone | 4 |
| Soy protein | 15 |
| Rice starch | 13 |
| Sericite GMS-4C | 10 |
| Pigment | 5 |
| Phase B | |
| Glycerin | 7 |

Example 6

| Inner core | |
|---|---|
| Phase A | |
| Candelilla | 2 |
| C20–40 Alcohols | 3 |
| Hydrogenated castor oil | 4 |
| PEG 400 Beeswax | 4 |
| Cetyl alcohol | 3 |
| Petrolatum | 4 |
| Silica | 1 |
| Palm oil | 4 |
| Polyethylene | 2 |
| Caprylic/Capric triglycerides | 10 |
| Octyl dodecanol | 12 |
| Triglycerol diisostearate | 2 |
| Castor oil | 12 |
| Rice starch | 15 |
| Karatin powder | 10 |
| Pigments | 10 |
| Phase B | |
| Glycerin | 2 |

Example 7

| Inner core | |
|---|---|
| Phase A | |
| Candelilla | 2 |
| C20–40 Alcohols | 3 |
| Hydrogenated castor oil | 4 |
| PEG 400 Beeswax | 4 |
| Cetyl alcohol | 3 |
| Petrolatum | 4 |
| Silica | 1 |
| Palm oil | 4 |
| Polyethylene | 2 |
| Caprylic/Capric triglycerides | 10 |
| Isopropyl isostearate | 4 |
| Octyl dodecanol | 8 |
| Glyceryl monostearate | 2 |
| Castor oil | 12 |
| Mica | 4 |
| Rice starch | 15 |
| Silk powder | 10 |
| Pigments | 6 |
| Phase B | |
| Glycerin | 2 |

Example 8

| Inner core | |
|---|---|
| Phase A | |
| Carnauba wax | 6 |
| Ozokerite | 19 |
| Oleyl alcohol | 49,7 |
| Propylene glycol | 2,3 |
| Castor oil | 5 |
| d-Iantrol | 5 |
| DC Red 21 | 0,4 |
| DC Red 7 lake | 0,6 |
| Black oxide | 1,1 |
| Ti-oxide | 2,5 |

-continued

| Inner core | |
|---|---|
| Red oxide | 2,3 |
| DC Red 6 | 0,1 |
| Tenox II | 0,1 |
| EO PA 54675 | 0,9 |
| Oleyl alcohol | 5 |

Working instruction for all examples

Place ingredients of the outer shell composition from phase A into a steam kettle and heat to 80–85° C., mix mechanically while heating. When phase A is melted and completely uniform, add phase B while mixing. Once uniform, the composition is poured into outer shell moulds at about 75° C. After withdrawing of the outer shell mould and the inner core insertion device and end of crystallization of the outer shell add the molten inner core composition into the cavity for inner core. Manufacturing procedures for the inner core compositions are the same as for the outer shell compositions.

What is claimed is:

1. Personal care product in the form of a free-standing stick, comprising of an inner core with cosmetic ingredients and an solid outer shell adhering to the inner core, in which the outer shell is wax-free and contains at least the following ingredients, in relation to the composition of the outer shell,
   (a) one or more solid proteins with a range of 0.5 to 50 weight %;
   (b) one or more liquid polyols or solutions of polyols with a range of 0.2 to 15 weight %;
   (c) one or more solid polyols with a range of 0.5 to 80 weight %;
   (d) one or more emollients with a range from 1 to 90 weight %;
   (e) additional cosmetic auxiliary materials and active ingredients with a range of between 0 and 80 weight %.

2. Product according to claim 1, wherein the protein is selected from the group consisting of soy protein, milk protein, oat protein, silk protein, pea protein, wheat protein, placental protein, collagen, rice protein, vegetable protein, wheat gluten, wheat germ protein, whey protein, potato protein, sweet almond protein, rice bran protein, yeast protein, keratin, corn protein, spinal protein, conchiorin protein, elastin, serum protein and their derivatives comprising hydrolyzed derivatives, ester derivatives, hydrogenated derivatives; and mixtures thereof.

3. Product according to claim 1, wherein the amount of the solid protein is in the range of 5 to 50% by weight.

4. Product according to claim 3, wherein the amount of the solid protein is in the range of 10 to 50% by weight.

5. Product according to claim 2, wherein the amount of the solid protein is in the range of 20 to 40% by weight.

6. Product according to claim 2, wherein the amount of the solid polyol is in the range of 15 to 70% by weight.

7. Product according to claim 6, wherein the amount of the solid polyol is in the range of 25 to 70% by weight.

8. Product according to claim 7, wherein the amount of the solid polyol is in the range of 30 to 70% by weight.

9. Product according to claim 1, wherein the liquid polyols or solutions of polyols for the outer shell are materials which include straight or branched chained hydrocarbon compounds, containing at least two hydroxyl groups on the carbon skeleton.

10. Product according to claim 1, wherein the outer shell, the inner core or both contains active skin-care ingredients, anti-oxidation agents, UV filters, moisturising agents, protective agents, perfume.

11. Product according to claim 1, wherein the ingredients of the outer shell as mixture have a drop melting point of above 105° C.

12. Product according to claim 1 wherein it is a lip stick.

* * * * *